United States Patent [19]
Kondo et al.

[11] 3,975,381
[45] Aug. 17, 1976

[54] PROCESS FOR PREPARING γ-LACTONE DERIVATIVES

[75] Inventors: Kiyosi Kondo, Yamato; Fumio Mori, Kawachinagano, Japan

[73] Assignee: Sagami Chemical Research Center, Tokyo, Japan

[22] Filed: Dec. 27, 1974

[21] Appl. No.: 536,781

[30] Foreign Application Priority Data
Dec. 27, 1973 Japan............................. 48-144501

[52] U.S. Cl................. 260/240 R; 260/240 D; 260/340.7; 260/343.6; 260/346.1 R; 260/410.9 R; 260/413; 260/473 A; 260/484 R; 260/615 A
[51] Int. Cl.².............. C07D 307/26; C07D 307/28; C07D 307/94
[58] Field of Search.......... 260/343.3, 343.6, 240 R, 260/240 D

[56] References Cited
UNITED STATES PATENTS

| | | | |
|---|---|---|---|
| 3,077,496 | 2/1963 | Julia.................................... | 260/514 |
| 3,299,100 | 1/1967 | Phillips........................... | 260/343.6 |

*Primary Examiner*—James A. Patten
*Attorney, Agent, or Firm*—Sughrue, Rothwell, Mion, Zinn & Macpeak

[57] ABSTRACT

A process for preparing a γ-lactone derivative having the formula (I)

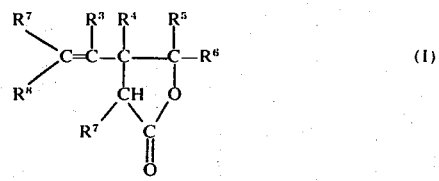

wherein $R^1$, $R^2$, $R^3$, $R^4$, $R^5$ and $R^6$, which may be the same or different, each represents a hydrogen atom, an alkyl group having 1 to 4 carbon atoms or a phenyl group which may be substituted with a halogen atom, and $R^1$ and $R^2$, and $R^5$ and $R^6$ may, when taken together with the carbon atom to which they are attached, form a cycloalkyl group having 4 to 7 carbon atoms, and $R^7$ represents a hydrogen atom, an alkyl group having 1 to 8 carbon atoms, a cycloalkyl group having 4 to 6 carbon atoms or a phenyl group which may be substituted with an alkyl group having 1 to 3 carbon atoms, which comprises reacting an allylic diol with an orthocarboxylic acid ester in the presence of an acidic catalyst.

8 Claims, No Drawings

PROCESS FOR PREPARING Γ-LACTONE DERIVATIVES

BACKGROUND OF THE INVENTION

1. Field of the Invention

This invention relates to a process for preparing γ-lactone derivatives. More particularly, this invention relates to a novel process for preparing γ-lactone derivatives having the formula (I)

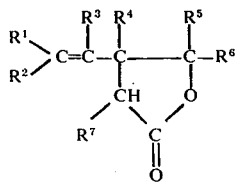

wherein $R^1$, $R^2$, $R^3$, $R^4$, $R^5$ and $R^6$, which may be the same or different, each represents a hydrogen atom, an alkyl group having 1 to 4 carbon atoms or a phenyl group which may be substituted with a halogen atom, and $R^1$ and $R^2$, and $R^5$ and $R^6$ may, when taken together with the carbon atom to which they are attached, form a cycloalkyl group having 4 to 7 carbon atoms, and $R^7$ represents a hydrogen atom, an alkyl group having 1 to 8 carbon atoms, a cycloalkyl group having 4 to 6 carbon atoms or a phenyl group which may be substituted with an alkyl group having 1 to 3 carbon atoms.

2. Description of the Prior Art

It is well known that β-isobutenylisohexano-γ-lactone (pyrocin) represented by the formula

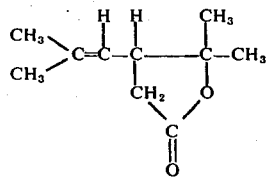

can be obtained by dry distillation of pyrethrum flowers (*Chrysanthemum cinerariaefolium*). Hitherto, it has been reported in the literature that pyrocin can be prepared by synthetic methods, for example, the method comprising reacting an acid chloride of terebic acid (i.e., γ,γ-dimethylparaconic acid) with isopropyl iodide [Matsui et al., *Bull. chem. Soc.*, Japan, 25, 210–214 (1952)], the method comprising pyrolysis of chrysanthemic acid in vacuo [L. Crombie et al., *J. Chrm. Soc.*, 470 (1954)], the method comprising reacting isobutenylacetone with ethyl bromoacetate and methyl magnesium iodide [M. Julia et al., *Compt. Rend.*, 251, 249–251 (1960)]. However, these known methods utilize starting materials which are extremely expensive and are not easily available and, further, the yield of the desired product, pyrocin, is said to be very low.

Also, it has been reported that pyrocin can be converted into crysanthemic acid or non-isoprenoid-type terpene alcohols by ring-opening of the lactone ring of pyrocin [Matsui et al., *Agr. Biol. Chem.*, 26, No. 8, 532–534 (1962) and W. Sucrow et al., *Tetrahedron Letters*, No. 42, 3675–3676 (1970)] and pyrocin per se possesses an insecticidal activity.

SUMMARY OF THE INVENTION

As a result of various studies on the process for preparing pyrocin as well as closely related γ-lactones which would be useful as insecticides, it was found that the γ-lactones represented by the formula (I) above can be prepared by a simple procedure and in high yield, as hereinafter described in greater detail, from starting materials which are easily available at low cost, i.e., from an allylic diol and an orthocarboxylic acid ester.

The γ-lactone derivatives of the formula (I) obtainable by the process of this invention are vinyl derivatives and therefore useful, in addition to the above-described utility, as starting materials for the synthesis of a wide variety of γ-lactone derivatives by utilizing well-established procedures for the reaction of a vinyl group. Also, the γ-lactone derivatives of the formula (I) can be used as a monomer for the production of vinyl-type polymers.

As is apparent from the structure of the formula (I), the γ-lactone derivatives obtainable by the process of this invention contain an unsaturated hydrocarbon group at the β-position of the lactone moiety thereof, and thus the present invention provides an easy and simple process for preparing such an unsaturated lactone derivative. The γ-lactone derivatives represented by the formula (I) above are novel compounds except for pyrocin [$R^1$, $R^2$, $R^5$ and $R^6$ are —$CH_3$; $R^3$ and $R^4$ are —H; and $R^7$ is —H in the formula (I)].

DETAILED DESCRIPTION OF THE INVENTION

The present invention provides a process for preparing a γ-lactone derivative having the formula (I)

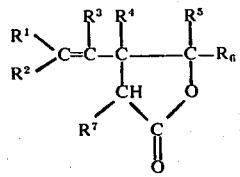

wherein $R^1$, $R^2$, $R^3$, $R^4$, $R^5$ and $R^6$, which may be the same or different, each represents a hydrogen atom, an alkyl group having 1 to 4 carbon atoms or a phenyl group which may be substituted with a halogen atom, and $R^1$ and $R^2$, and $R^5$ and $R^6$ may, when taken together with the carbon atom to which they are attached, form a cycloalkyl group having 4 to 7 carbon atoms, and $R^7$ represents a hydrogen atom, an alkyl group having 1 to 8 carbon atoms, a cycloalkyl group having 4 to 6 carbon atoms or a phenyl group which may be substituted with an alkyl group having 1 to 3 carbon atoms, which comprises reacting an allylic diol having the formula (II)

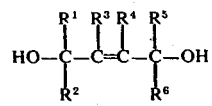

Wherein $R^1$, $R^2$, $R^3$, $R^4$, $R^5$ and $R^6$ are as defined above, with an orthocarboxylic acid ester having the formula (III)

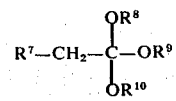

wherein $R^7$ is as defined above and $R^8$, $R^9$ and $R^{10}$, which may be the same or different, each represents an alkyl group having 1 to 5 carbon atoms or a cycloalkyl group having 4 to 6 carbon atoms, in the presence of an acidic catalyst.

The term "alkyl group having 1 to 3 carbon atoms" used herein designates a straight or branched chain alkyl group having 1 to 3 carbon atoms, e.g., a methyl, ethyl, n-propyl or isopropyl group.

The term "alkyl group having 1 to 4 carbon atoms" used herein designates a straight or branched chain alkyl group having 1 to 4 carbon atoms, for example, a methyl, ethyl, n-propyl, isopropyl, n-butyl, sec-butyl or tert-butyl group.

The term "alkyl group having 1 to 5 carbon atoms" used herein designates a straight or branched chain alkyl group having 1 to 5 carbon atoms, for example, those given for the above alkyl groups and a pentyl group.

The term "alkyl group having 1 to 8 carbon atoms" used herein designates a straight or branched chain alkyl group having 1 to 8 carbon atoms, for example, those given for the above alkyl groups and a hexyl, heptyl or octyl group.

The term "halogen atom" used herein designates a fluorine, chlorine, bromine or iodine atom.

The term "cycloalkyl group having 4 to 6 carbon atoms" used herein designates a cyclobutyl, cyclopentyl or cyclohexyl group.

The term "cycloalkyl group having 4 to 7 carbon atoms" used herein designates a cyclobutyl, cyclopentyl, cyclohexyl or cycloheptyl group.

The term "phenyl group which may be substituted with a halogen atom" used for $R^1$ to $R^6$ designates, for example, a phenyl group, a p-bromophenyl, and the like.

The term "phenyl group which may be substituted with an alkyl group having 1 to 3 carbon atoms" used for $R^7$ designates, for example, an unsubstituted phenyl group, a m-tolyl group, an o-tolyl group, and the like.

Suitable examples of the allylic diols of the formula (II) which can be used in the present invention are 2-butene-1,4-diol, 2-pentene-1,4-diol, 3-hexene-2,5-diol, 3-heptene-2,5-diol, 4-octene-3,6-diol, 2-methyl-2-butene-1,4-diol, 2,3-dimethyl-2-butene-1,4-diol, 4-methyl-2-pentene-1,4-diol, 5-methyl-3-hexene-2,5-diol, 2,3,5-trimethyl-3-hexene-2,5-diol, 4-ethyl-2-hexene-1,4-diol, 1-phenyl-2-butene-1,4-diol, 1,4-diphenyl-2-butene-1,4-diol, 2,5-dimethyl-3-hexene-2,5-diol, 3,6-dimethyl-4-octene-3,6-diol, 2,4,7,9-tetramethyl-5-decene-4,7-diol, 2,5,7-trimethyl-3-octene-2,5-diol, 1,2-bis(1-hydroxy-1-cyclohexyl)-ethylene, 4,4-diphenyl-2-butene-1,4-diol, 4,4-bis(p-bromophenyl)-2-butene-1,4-diol, and the like.

The allylic diols of the formula (II) used in the present invention are present as geometric isomers, i.e., a trans-form and a cis-form as illustrated below:

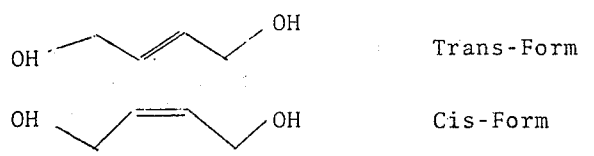

Trans-Form

Cis-Form

Either of the trans-form or the cis-form can be used in the present invention, but it is advantageous to use the trans-form in order to improve the yield of the desired product. When the starting material of the formula (II) is in the cis-form, there is occasionally observed the formation of undesired by-products.

Suitable examples of the orthocarboxylic acid esters of the formula (III) which can be used in the present invention are 1,1,1-trimethoxyethane, 1,1,1-triethoxyethane, 1,1,1-tripropyloxyethane, 1,1,1-tricyclohexyloxyethane, 1,1,1-tri(n-butyloxy)ethane, 1,1,1-triethoxypropane, 1,1,1-triethoxybutane, 1,1,1-triethoxypentane, 3-methyl-1,1,1-triethoxybutane, 3,7-dimethyl-1,1,1-triethoxyoctane, 2-phenyl-1,1,1-triethoxyethane, 2-(o-methylphenyl)-1,1,1-triethoxyethane, 2-(m-methylphenyl)-1,1,1-triethoxyethane, 2-cyclohexyl-1,1,1-trimethoxyethane, 1,1-di-methoxy-1-cyclohexyloxyethane, 1,1-dimethoxy-1-pentoxyethane, and the like, and the corresponding ketene acetals thereof.

The acidic catalyst which can be used in the present invention is phenols such as phenol, o-, m- and p-nitrophenols, o-, m- and p-cresols, o-, m- and p-xylenols, 2,6-dimethylphenol, 2,6-di-tert-butylphenol, 2,4,6-trisec-butylphenol, 2,4,6-tri-tert-butylphenol, 4-methyl-2,6-di-tert-butylphenol, 4-methyl-3,5-di-tert-butylphenol, hydroquinone, 2,5-di-tert-butylhydroquinone α,β-naphthols and the like; aliphatic carboxylic acids having 2 to 10 carbon atoms such as acetic acid, propionic acid, butyric acid, isobutyric acid, cyclohexanecarboxylic acid, valeric acid, malonic acid, succinic acid, adipic acid and the like; benzoic acids such as benzoic acid, m-chlorobenzoic acid and the like; sulfonic acids such as benzenesulfonic acid, p-toluenesulfonic acid and the like; inorganic acids such as hydrochloric acid, sulfuric acid, phosphoric acid, boric acid and the like; and Lewis acids such as aluminum chloride, stannic chloride, zinc chloride, ferric chloride, boron trifluoride, mercuric acetate and the like. It is preferred to use the above phenols, aliphatic acids, particularly those having 2 to 6 carbon atoms, and benzoic acids as acidic catalysts in order to minimize side-reactions such as dehydration of the allylic diols of the formula (II) used as a starting material. The acidic catalyst can be generally used in an amount of from about 0.001 to about 20% by weight, preferably 1 to 15% by weight, based on the weight of the allylic diol reactant used.

The reaction between the allylic diol of the formula (II) and the orthocarboxylic acid ester of the formula (III) can be carried out in the absence of any reaction solvent, but solvents which are inert to the reactants and the product can be used in the reaction. Suitable examples of the solvents are n-octane, toluene, o-, m- and p-xylene, di-n-butyl ether, N,N-dimethylformamide, etc., preferably o-, m- and p-xylenes. Alternatively, an excess amount of the orthocarboxylic acid ester of the formula (III) can be used as both a reactant and a reaction solvent.

The above reaction can be generally carried out in a molar ratio of about 1 to about 5 moles, preferably 1 to 2 moles, of the orthocarboxylic acid ester (III) per mole of the allylic diol (II), regardless of the presence or absence of reaction solvents. The reaction temperature is not critical, but it is preferred to carry out the reaction at a temperature of from about 100° to about 250°C, preferably from 120° to 180°C, for a period of from about 2 to about 48 hours, preferably 6 to 24 hours, from the standpoints of the reaction rate and the yield of the desired product. As is apparent to one skilled in the art, the higher the temperature, the shorter the reaction time.

The reaction can be advantageously carried out while continuously removing the alcohol formed during the reaction out of the reaction system as is described hereinafter in greater detail. The removal of the alcohol from the reaction system can easily be attained by distillation. Neither pressurized nor inert atmospheric condition is necessary for the reaction.

A typical embodiment of the reaction according to the process of this invention is illustrated by the following sequences of teh reaction using trans-2-butene-1,4-diol as allylic diol (II) and a 1,1,1-triethoxy compound as an orthocarboxylic acid ester, but the present invention is not limited to the specific embodiment. Also, the reaction mechanism of the process of this invention is not bound by the specific sequences of the reaction shown below. In the sequences of the reaction given below, the group $R^7$ has the same meaning as above.

In the above sequences of reaction, the diol (II) reacts with the orthocarboxylic acid ester (III) in the form of $R^7$—CH=C(OC$_2$H$_5$)$_2$ (III') (as described hereinafter) in the presence of an acidic catalyst while releasing one molecule of ethanol to form the compound of the formula (IV) [Reaction (1)]. The compound of the formula (IV) releases an additional one molecule of ethanol in the presence of the acidic catalyst to form the compound of the formula (V) [Reaction (2)]. The compound of the formula (V) undergoes the Claisen-type rearrangement as shown by the dotted arrow line and at the same time is split as shown by the dotted line

Sequences of Reaction

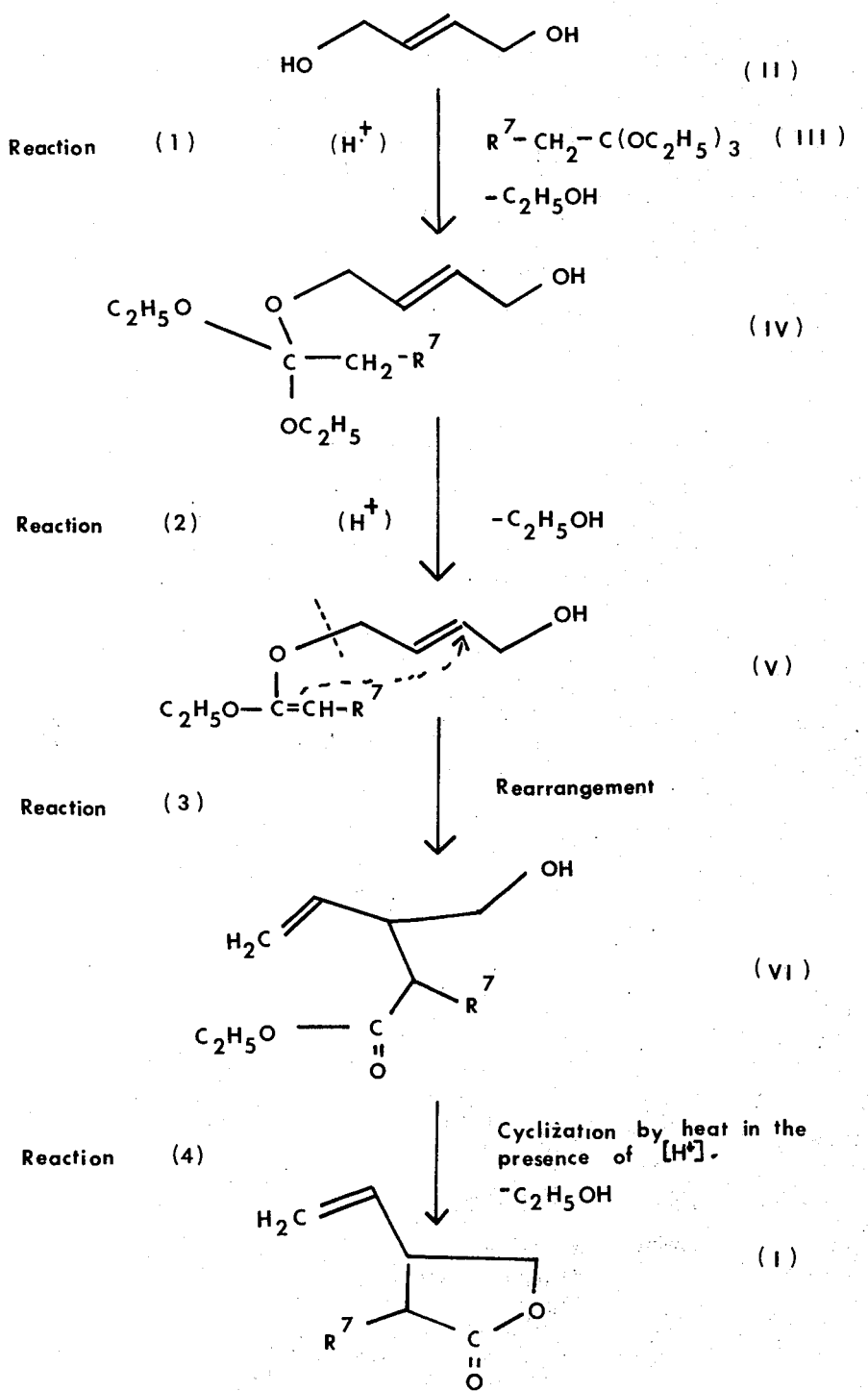

to form the compound of the formula (VI) [Reaction (3)]. The compound of the formula (VI) is then cyclized in the presence of an acidic catalyst under the reaction condition, releasing an additional one molecule of ethanol to form the desired γ-lactone of the formula (I).

A series of reactions indicated by Reaction (1) through Reaction (4) occurs in sequence in a single reaction system containing an acidic catalyst and therefore it is not necessary to isolate the intermediates formed in each of the sequences or to carry out Reactions (1), (2), (3) and (4) in separate steps. However, in order to ensure a smooth reaction in Reactions (1), (2) and (4), it is preferred to remove the alcohol formed during the reaction. In particular, it is advantageous to shift the equilibrium between the compound (III) and the compound (III') to the side of the compound (III') by distilling off the alcohol formed in Reaction (1) from the reaction system. The equilibrium between the compound (III) and compound compoune (III') can be shown as follows:

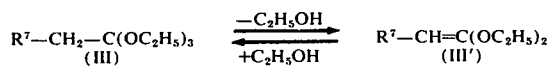

The present invention is further illustrated in greater detail by the following Examples, but these Examples are given for illustrative purposes only and not to be construed as limiting the scope of the invention. Unless otherwise indicated, all parts, percents, ratios and the like are by weight.

EXAMPLE 1

0.9 Part of isobutyric acid was added in small portions to a mixture of 8.8 parts of trans-2-butene-1,4-diol and 32.4 parts of ethyl orthoacetate while maintaining the mixture at a temperature of 130° to 140°C, and the resulting mixture was stirred for 12 hours while distilling off the ethanol formed during the reaction from the reaction system. Thereafter, the reaction mixture was distilled under reduced pressure to afford the desired product, β-vinyl-γ-butyrolactone, as an oily fraction boiling at a temperature between 92° and 98°C. The yield of the product thus obtained was found to be 62%. The product showed the following characteristics.

NMR Spectral Analysis (δ ppm): 2.0–2.9 (d AB q) 2H, 3.20(m) 1H, 3.8–4.6(m) 2H, 5.0–6.2(m) 3H.

IR Spectral Analysis (neat): 1780 cm$^{-1}$ (>C=O)

Mass Spectrum: m/e 112

EXAMPLE 2

A mixture of 14.4 parts of trans-2,5-dimethyl-3-hexene-2,5-diol, 32.4 parts of ethyl orthoacetate and 1.4 parts of phenol was stirred for 24 hours at a temperature of 140° to 150°C while distilling off the ethanol formed during the reaction from the reaction system. The reaction mixture was then distilled under reduced pressure to afford the desired product, β-isobutenyl-γ-isohexanolactone (pyrocin) as a fraction boiling at a temperature of 128° to 130°C at 14 mmHg, which solidified. The yield of the product thus obtained was found to be 80%. The product showed the following characteristics:

Melting Point: 58.5°–59°C.

NMR Spectral Analysis (δ ppm): 1.22(s) 3H, 1.37(s) 3H, 1.70(bs) 3H, 1.76(bs) 3H, 2.1–2.5(m) 2H, 2.6–3.4(m) 1H, 5.03(bd, J=9 cps) 1H.

IR Spectral Analysis (nujol): 1785, 1765 cm$^{-1}$ (>C=O)

Elementary Analysis (theoretical values in brackets): C(%), 71.13 (71.39); H(%), 9.53 (9.59).

EXAMPLE 3

The reaction was carried out in the same manner as described in Example 1 but using cis-2-butene-1,4-diol in place of trans-2-butene-1,4-diol. The reaction mixture was found to contain β-vinyl-γ-butyrolactone in a yield of about 10% by gas chromatography and also contained predominantly 2-methyl-2-ethoxy-1,3-dioxa-5-cycloheptene [CH$_3$C(OC$_2$H$_5$).(OCH$_2$CH=CHCH$_2$O)] having a boiling point of 76°–84°C at 14 mmHg.

Also, when cis-2,5-dimethyl-3-hexene-2,5-diol was used as a diol reactant in the above reaction, β-isobutenylisohexano-γ-lactone was obtained in a yield of about 10%.

EXAMPLE 4

The reaction was carried out in the same manner as described in Example 2 but using 4.9 parts of trans-2,5-diemthyl-3-hexene-2,5-diol, 12.0 parts of ethyl orthopropionate and 0.5 part of phenol to afford an oily fraction having a boiling point of 72°–74°C at 0.07 mmHg. The resulting fraction was found to contain the desired product α-methyl-β-isobutenyl-γ-isohexanolactone in a yield of about 50% and other by-products by gas chromatography and NMR spectral analysis.

EXAMPLE 5

A mixture of 5.1 parts of trans-2-methyl-2-butene-1,4-diol, 16.2 parts of ethyl orthoacetate and 0.5 part of hydroquinone was allowed to react in the same manner as described in Example 2 and an oily fraction having a boiling point of 99°–108°C at 11 mmHg was recovered, which was found to be a mixture comprising an approximately equal amount of a γ-lactone (A) having the formula (I) wherein $R^1$, $R^2$, $R^3$, $R^5$, $R^6$ and $R^7$ represent hydrogen atoms and $R^4$ represents a methyl group, and a γ-lactone (B) having the formula (I) wherein $R^1$, $R^2$, $R^4$, $R^5$, $R^6$ and $R^7$ represent hydrogen atoms and $R^3$ represents a methyl group, in a yield of about 81%. The mixture thus obtained showed the following characteristics:

IR Spectral Analysis (neat): 1780 cm$^{-1}$ (>C=O)

Mass Spectrum: m/e 126(M$^+$)

Elementary Analysis (theoretical values in brackets): C(%), 66.68 (66.64); H(%), 8.00 (7.99).

NMR Spectral Analysis (δ ppm): Product (A): 1.28(s) CH$_3$, 2.0–2.7(m) —CH$_2$—COO—, 3.8–4.5(m) —CH$_2$O—, 4.9–6.1(m) CH$_2$=CH—. Product (B): 1.76(s) CH$_3$, 2.0–2.7(m) —CH$_2$—COO—, 2.9–3.4(m) —CH, 3.8–4.5(m) —CH$_2$O—, 4.83(bs) CH$_2$=C<.

EXAMPLE 6

A mixture of 2.6 parts of trans-2-methyl-3-pentene-2,5-diol, 7.3 parts of ethyl orthoacetate and 0.3 part of hydroquinone was allowed to react in the same manner as described in Example 2 and an oily fraction having a boiling point of 77°–80°C at 2 mmHg was recovered to produce a γ-lactone having the formula (I) wherein $R^1$, $R^2$, $R^3$, $R^4$ and $R^7$ represent hydrogen atoms and $R^5$ and $R^6$ represent methyl groups in a yield of about 91%. The product thus obtained showed the following characteristics:

IR Spectral Analysis (neat): 1780 cm$^{-1}$ (>C=O)

Mass Spectrum: m/e 140 (M$^+$)

Elementary Analysis (theoretical values in brackets):
C(%), 68.74 (68.54); H(%), 8.64(8.63)

NMR Spectral Analysis (δ ppm): 1.20(s) 3H, 1.40(s) 3H, 2.2–3.1(m) 3H, 4.9–6.1(m) 3H.

EXAMPLE 7

A mixture of 4.6 parts of trans-3-hexene-2,5-diol, 13.0 parts of ethyl orthoacetate and 0.5 part of hydroquinone was allowed to react in the same manner as described in Example 2 and an oily fraction having a boiling point of 56°–60°C at 0.15 mmHg was recovered to obtain a γ-lactone product (a mixture of cis and trans forms) having the formula (I) wherein $R^2$, $R^3$, $R^4$, $R^6$ and $R^7$ represent hydrogen atoms and $R^1$ and $R^5$ represent methyl groups in a yield of about 52%. The product thus obtained showed the following characteristics:

IR Spectral Analysis (neat): 1765, 1785 cm$^{-1}$ (>C=O)

Mass Spectrum: m/e 140 (M$^+$)

Elementary Analysis (theoretical values in brackets): C(%), 68.58 )68.54); H(%), 8.52 (8.63)

NMR Spectral Analysis (δ ppm): 1.28(s), 1.39(s) 3H; 1.65(s), 1.72(s) 3H; 2.1–2.9(m) 2H, 3.8–4.3(m) 1H, 5.0–5.9(m) 2H.

EXAMPLE 8

A mixture of 8.8 parts of trans-2-butene-1,4-diol, 32.4 parts of ethyl orthoacetate and 0.9 part of hydroquinone was allowed to react in the same manner as described in Example 2 and a fraction having a boiling point of 106°–107°C at 22 mmHg was recovered to afford β-vinyl-γ-butyrolactone having the formula (I) wherein $R^1$, $R^2$, $R^3$, $R^4$, $R^5$, $R^6$ and $R^7$ represent hydrogen atoms in a yield of 89%.

Elementary Analysis (theoretical values in brackets): C(%), 64.36 (64.27); H(%), 7.01 (7.19).

EXAMPLE 9

A mixture of 4.3 parts of cis-2,5-dimethyl-3-hexene-2,5-diol, 9.7 parts of ethyl orthoacetate and 0.4 parts of hydroquinone was allowed to react in the same manner as described in Example 2 to obtain β-isobutenyl-γ-isohexanolactone having the formula (I) wherein $R^3$, $R^4$ and $R^7$ represent hydrogen atoms and $R^1$, $R^2$, $R^5$ and $R^6$ represent methyl groups in a yield of 30%. In this Example, the conversion of the reactant was found to be low, and the unreacted diol was recovered. Also, a small amount of 2,2,5,5-tetramethyl-2,5-dihydrofuran was found to be produced.

EXAMPLE 10

A mixture of 8.8 parts of cis-2-butene-1,4-diol, 32.4 parts of ethyl orthoacetate and 0.9 part of hydroquinone was allowed to react in the same manner as described in Example 2 to obtain β-vinyl-γ-butyrolactone in a yield of 45%. In this Example, 2-methyl-2-ethoxy-1,3-dioxa-5-cycloheptene which was formed as by-product in Example 3 was found to be produced in a yield of 19%.

While the invention has been described in greater detail with reference to specific embodiments thereof, it will be apparent to one skilled in the art that various changes and modifications can be made therein without departing from the scope and spirit of the invention.

What is claimed is:

1. A process for preparing a γ-lactone derivative having the formula (I)

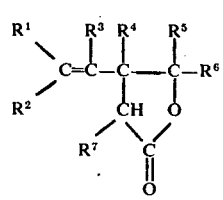

wherein $R^1$, $R^2$, $R^3$, $R^4$, $R^5$ and $R^6$, which may be the same or different, each represents a hydrogen atom, an alkyl group having 1 to 4 carbon atoms or phenyl group which may be substituted with a halogen atom, and $R^1$ and $R^2$, and $R^5$ and $R^6$ may, when taken together with the carbon atom to which they are attached, form a cycloalkyl group having 4 to 7 carbon atoms, and $R^7$ represents a hydrogen atom, an alkyl group having 1 to 8 carbon atoms, a cycloalkyl group having 4 to 6 carbon atoms, a phenyl group which may be substituted with an alkyl group having 1 to 3 carbon atoms, which comprises reacting an allylic diol having the formula (II)

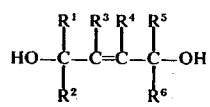

wherein $R^1$, $R^2$, $R^3$, $R^4$, $R^5$ and $R^6$ are as defined above, with an orthocarboxylic acid ester having the formula (III)

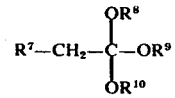

wherein $R^7$ is as defined above and $R^8$, $R^9$ and $R^{10}$, which may be the same or different, each represents an alkyl group having 1 to 5 carbon atoms or a cycloalkyl group having 4 to 6 carbon atoms, in the presence of an acidic catalyst.

2. A process according to claim 1, wherein said orthocarboxylic acid ester of the formula (III) is used in a molar ratio of about 1 to about 5 moles per mole of said allylic diol of the formula (II).

3. A process according to claim 1, wherein said reaction is conducted at a temperature of from about 100°C to about 250°C for a period of from about 2 to about 48 hours.

4. A process according to claim 1, wherein said reaction is conducted while continuously removing the alcohol formed during the reaction from the reaction system.

5. A process according to claim 1, wherein said acidic catalyst is present in the reaction system in an amount of from about 0.001 to about 20% by weight based on the weight of said allylic diol of the formula (II).

6. A process according to claim 1, wherein said reaction is conducted in the absence of reaction solvents.

7. A process according to claim 1, wherein said reaction is conducted in the presence of an inert solvent.

8. A process according to claim 1, wherein said acidic catalyst is selected from the group consisting of phenols, aliphatic carboxylic acids having 2 to 10 carbon atoms and benzoic acids.

* * * * *